(12) United States Patent
Gettings et al.

(10) Patent No.: US 10,143,982 B2
(45) Date of Patent: *Dec. 4, 2018

(54) MIXING SYSTEM AND VALVE ASSEMBLY (71) Applicant: Orthovita, Inc., Malvern, PA (US)

(72) Inventors: John A. Gettings, Drexel Hill, PA (US); Matthew B. Havener, Conshohocken, PA (US); Stephen E. McIlhenny, Lansdale, PA (US)

(73) Assignee: Orthovita, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/687,879

(22) Filed: Aug. 28, 2017

(65) Prior Publication Data

US 2017/0354938 A1 Dec. 14, 2017

Related U.S. Application Data (60) Continuation of application No. 15/424,150, filed on Feb. 3, 2017, now Pat. No. 9,776,150, which is a
(Continued)

(51) Int. Cl.
*B01F 5/06* (2006.01)
*B01F 13/00* (2006.01)
(Continued)

(52) U.S. Cl.
CPC .......... *B01F 13/0023* (2013.01); *A61L 27/10* (2013.01); *A61L 27/12* (2013.01);
(Continued)

(58) Field of Classification Search
CPC .................................................... B01F 5/0685
(Continued)

(56) References Cited

U.S. PATENT DOCUMENTS

| 289,637 | A | * | 12/1883 | Fitzgerald | B60K 15/06 137/583 |
| 305,831 | A | * | 9/1884 | McAurthur | B60T 15/043 303/50 |

(Continued)

FOREIGN PATENT DOCUMENTS

| DE | 10333384 A1 | 2/2005 |
| EP | 0497576 A1 | 8/1992 |

(Continued)

OTHER PUBLICATIONS

Stryker, Vitoss, Bone Graft Substitute, Aug. 2011, 8 pages.

*Primary Examiner* — David L Sorkin
(74) *Attorney, Agent, or Firm* — Lerner, David, Littenberg, Krumholz & Mentlik, LLP (57) ABSTRACT

A mixing system is disclosed in which the system comprises a source of bone-graft or bone-graft-substitute material, a liquid source, and a vacuum source, at least one of the source of bone-graft or bone-graft-substitute material and the liquid source being in communication with the vacuum source. A valve assembly also forms part of the system, the valve assembly having a valve movable between a first position in which a first fluid passageway is created between the source of bone-graft or bone-graft-substitute material and the vacuum, and a second position in which a second fluid passageway is created between the source of bone-graft or bone-graft-substitute material and the liquid source, wherein, in the second position, the valve seals off the first fluid passageway, the vacuum source being adapted to generate a negative-pressure environment, relative to atmospheric pressure, within the valve assembly while the valve is in the first position. Methods of utilizing the aforementioned system are also disclosed.

9 Claims, 11 Drawing Sheets

Related U.S. Application Data division of application No. 14/190,484, filed on Feb. 26, 2014, now Pat. No. 9,604,184.

(60) Provisional application No. 61/773,385, filed on Mar. 6, 2013.

(51) Int. Cl.

| | | |
|---|---|---|
| *A61L 27/10* | (2006.01) | |
| *A61L 27/12* | (2006.01) | |
| *A61L 27/22* | (2006.01) | |
| *A61L 27/24* | (2006.01) | |
| *A61L 27/38* | (2006.01) | |
| *A61L 27/54* | (2006.01) | |
| *B01F 15/02* | (2006.01) | |

(52) U.S. Cl.
CPC ............. *A61L 27/222* (2013.01); *A61L 27/24* (2013.01); *A61L 27/3821* (2013.01); *A61L 27/54* (2013.01); *B01F 5/0685* (2013.01); *B01F 15/0258* (2013.01); *A61L 2300/112* (2013.01); *A61L 2430/02* (2013.01); *B01F 2215/0029* (2013.01); *B01F 2215/0032* (2013.01); *Y10T 137/0318* (2015.04); *Y10T 137/8766* (2015.04)

(58) Field of Classification Search
USPC .............................. 366/139, 189; 137/625.47
See application file for complete search history.

(56) References Cited

U.S. PATENT DOCUMENTS

| | | | |
|---|---|---|---|
| 1,077,697 A * | 11/1913 | Gates ................. | F16K 11/0853 137/625.47 |
| 1,381,129 A * | 6/1921 | Maul ....................... | F24C 3/128 137/625.47 |
| 1,496,259 A * | 6/1924 | Fairlie ..................... | F16K 31/60 116/277 |
| 2,520,957 A | 9/1950 | Peterson | |
| 4,743,229 A | 5/1988 | Chu | |
| 4,982,760 A * | 1/1991 | Mustaklem ......... | F16K 11/0853 137/559 |
| 5,098,405 A | 3/1992 | Peterson et al. | |
| 5,181,909 A | 1/1993 | McFarlane | |
| 5,334,159 A | 8/1994 | Turkel | |
| 5,609,584 A | 3/1997 | Gettig et al. | |
| 5,827,941 A | 10/1998 | Good et al. | |
| 5,839,715 A | 11/1998 | Leinsing | |
| 6,096,309 A | 8/2000 | Prior et al. | |
| 6,234,196 B1 | 5/2001 | Fischer et al. | |
| 6,280,727 B1 | 8/2001 | Prior et al. | |
| 6,349,850 B1 | 2/2002 | Cheikh | |
| 6,383,519 B1 | 5/2002 | Sapieszko et al. | |
| 6,521,246 B2 | 2/2003 | Sapieszko et al. | |
| 6,568,439 B1 | 5/2003 | Se et al. | |
| 6,607,508 B2 | 8/2003 | Knauer | |
| 6,616,627 B2 | 9/2003 | Willis et al. | |
| 6,656,163 B1 | 12/2003 | Marshall et al. | |
| 6,681,810 B2 | 1/2004 | Weston | |
| 6,709,149 B1 | 3/2004 | Tepic | |
| 6,723,131 B2 | 4/2004 | Muschler | |
| 6,955,660 B2 | 10/2005 | Fisher | |
| 7,073,936 B1 | 7/2006 | Jonsson | |
| 7,189,263 B2 | 3/2007 | Erbe et al. | |
| 7,198,150 B1 | 4/2007 | Blaschke et al. | |
| 7,328,549 B2 | 2/2008 | Kinney et al. | |
| 7,497,843 B1 | 3/2009 | Castillo et al. | |
| 7,503,906 B2 | 3/2009 | Nemoto | |
| 7,531,004 B2 | 5/2009 | Bagga et al. | |
| 7,578,803 B2 | 8/2009 | Rome et al. | |
| 7,670,384 B2 | 3/2010 | Kumar et al. | |
| 7,731,679 B2 | 6/2010 | Tennican et al. | |
| 7,806,856 B2 | 10/2010 | Bagaoisan et al. | |
| 7,828,780 B2 | 11/2010 | Chu et al. | |
| 7,850,646 B2 | 12/2010 | Segal | |
| 7,878,704 B2 | 2/2011 | Bonnard | |
| 7,882,863 B2 | 2/2011 | Pestotnik et al. | |
| 8,297,831 B2 | 10/2012 | Lidgren et al. | |
| 8,303,967 B2 | 11/2012 | Clineff et al. | |
| 8,308,340 B2 | 11/2012 | Ferrante et al. | |
| 8,317,741 B2 | 11/2012 | Kraushaar | |
| 8,540,723 B2 | 9/2013 | Shadduck et al. | |
| 8,668,375 B2 | 3/2014 | Hawkins et al. | |
| 9,107,668 B2 | 8/2015 | Melsheimer et al. | |
| 9,132,573 B2 | 9/2015 | Vogt et al. | |
| 9,180,416 B2 | 11/2015 | Phan et al. | |
| 9,427,715 B2 | 8/2016 | Palazzolo et al. | |
| 9,776,150 B2 * | 10/2017 | Gettings ............... | B01F 5/0685 |
| 2001/0016703 A1 | 8/2001 | Wironen et al. | |
| 2001/0037091 A1 | 11/2001 | Wironen et al. | |
| 2005/0087715 A1 | 4/2005 | Doyle | |
| 2005/0209555 A1 | 9/2005 | Middleton et al. | |
| 2007/0088252 A1 | 4/2007 | Pestotnik et al. | |
| 2008/0066816 A1 | 3/2008 | Steppe et al. | |
| 2008/0086093 A1 | 4/2008 | Steppe et al. | |
| 2008/0287906 A1 | 11/2008 | Burkholz et al. | |
| 2009/0275901 A1 | 11/2009 | Mckinnon | |
| 2009/0287154 A1 | 11/2009 | Harding et al. | |
| 2010/0008181 A1 | 1/2010 | Lidgren et al. | |
| 2010/0091606 A1 | 4/2010 | Kwan et al. | |
| 2012/0071884 A1 | 3/2012 | Cooper et al. | |
| 2012/0279884 A1 | 11/2012 | Tennican et al. | |
| 2014/0261082 A1 | 9/2014 | Anderson et al. | |
| 2014/0323662 A1 | 10/2014 | Kwan et al. | |
| 2016/0157910 A1 | 6/2016 | Phan et al. | |

FOREIGN PATENT DOCUMENTS

| | | |
|---|---|---|
| EP | 0856331 A2 | 8/1998 |
| EP | 1211184 A1 | 6/2002 |
| EP | 1616808 A1 | 1/2006 |
| EP | 1827567 A1 | 9/2007 |
| EP | 2063932 A2 | 6/2009 |
| EP | 2069580 A2 | 6/2009 |
| EP | 2079501 A2 | 7/2009 |
| EP | 2291216 A1 | 3/2011 |
| EP | 2307087 A1 | 4/2011 |
| FR | 438652 A | 5/1912 |
| GB | 191202554 A | 5/1912 |
| SE | 500430 C2 | 6/1994 |

* cited by examiner

MIXING SYSTEM AND VALVE ASSEMBLY

CROSS-REFERENCE TO RELATED APPLICATIONS

This application is a continuation of U.S. application Ser. No. 15/424,150, filed on Feb. 3, 2017, which is a divisional of U.S. application Ser. No. 14/190,484, filed on Feb. 26, 2014, which claims the benefit of U.S. Provisional Patent Application No. 61/773,385, filed Mar. 6, 2013, the disclosures of which are incorporated herein by reference.

BACKGROUND OF THE INVENTION

The present invention(s) relates to apparatus and methods for mixing certain substances, particularly substances usable for repairing or grafting bone.

Bone-graft or bone-graft-substitute materials are used in many applications within the orthopedic and/or other medical fields, such as to cause fusion of adjacent bone parts to repair a fracture, to fuse a joint(s) and alleviate pain at the joint(s), or more securely attach an implant or other device to bone. Indeed, such bone-graft or bone-graft-substitute materials have numerous indications within the orthopedic field, which rely on the ability of the material to induce natural bone growth at the repair site (e.g., for regenerating and/or forming additional bone at the site). As an example, a bone-graft substitute currently offered by Orthovita, Inc., the assignee of the present application, comprises, in some cases, β-TCP (i.e., beta tri-calcium phosphate), collagen, and/or bioactive glass. The bone-graft substitute, which is referred to as Vitoss® (manufactured by Orthovita, Inc., Malvern, Pa.) in the industry, has been shown to have superior bone affinity and growth properties, and is used in various different contexts, such as a bone-void filler for voids or gaps in trauma applications.

In the case of bone-graft or bone-graft-substitute material, it is also sometimes preferable to mix such material with other compositions so that the maximum effect is achieved. The other components of the mixture may be a liquid, such as bone marrow aspirate, blood, saline, and/or water. In the case of Vitoss®, when mixed with bone marrow, such bone-graft substitute has proven a clinically effective autograft replacement. Thus, Vitoss® is able to replicate natural bone taken directly from the patient. In any case, prior to application of certain bone-graft or bone-graft-substitute materials, a surgeon, nurse, or other skilled operator (hereinafter "the user") might be required to mix the various components of the material so that, once applied to bone, the material induces the most-efficient bone formation.

While numerous mixing devices have been created for mixing bone-graft or bone-graft-substitute components, most require too many steps or are ineffective in their application. Thus, there exists a need for an improved mixing system allowing for efficient mixing of the components of different bone-graft and bone-graft-substitute materials.

BRIEF SUMMARY OF THE INVENTION

One aspect of the present invention provides a method of mixing bone-graft or bone-graft-substitute material with one or more other components. The method may comprise: (1) providing a source of bone-graft or bone-graft-substitute material, and a source of liquid, at least one of the source of bone-graft or bone-graft-substitute material and the liquid source being in communication with a vacuum source; (2) moving a valve so that a first fluid passageway between the vacuum source and the source of bone-graft or bone-graft-substitute material is opened; (3) using the vacuum source to create a vacuum between the source of bone-graft or bone-graft-substitute material and the vacuum source, the vacuum generating negative pressure, relative to atmospheric pressure, within the first fluid passageway; (4) sealing the first fluid passageway to maintain the vacuum within the source of bone-graft or bone-graft-substitute material; and (5) moving the valve so that a second fluid passageway between the source of bone-graft or bone-graft-substitute material and the liquid source is opened, wherein liquid from the liquid source is drawn into the second fluid passageway and to the source of bone-graft or bone-graft-substitute material via the negative pressure generated during the using step. The steps of the method, of course, may take place in another order besides that set forth above.

In certain embodiments of this aspect, the method may also comprise providing a valve assembly having internal channels that facilitate creation of the first and second fluid passageways, wherein at least some of the internal channels house the valve. In addition, the source of bone-graft or bone-graft-substitute material, the liquid source, and the vacuum source may all be syringes connected to a valve assembly containing the valve. What is more, the bone-graft or bone-graft-substitute material may comprise natural bone particles, particles of β-TCP, or hydroxyapatite combined with β-TCP, each of such materials optionally including bioactive glass, and the liquid source may comprise water, saline, blood, bone marrow aspirate, or a combination thereof. The bone-graft or bone-graft-substitute material can further be mixed with gelatin, collagen, micro-fibrillar collagen, or a combination thereof.

Another aspect of the invention includes a system for mixing a bone-graft or bone-graft-substitute material with one or more other components, the system comprising: (1) a source of bone-graft or bone-graft-substitute material, a liquid source, and a vacuum source, at least one of the source of bone-graft or bone-graft-substitute material and the liquid source being in communication with the vacuum source; and (2) a valve assembly having a valve movable between a first position in which a first fluid passageway is created between the source of bone-graft or bone-graft-substitute material and the vacuum, and a second position in which a second fluid passageway is created between the source of bone-graft or bone-graft-substitute material and the liquid source. The valve according to this aspect, in the second position, may also seal off the first fluid passageway, and the vacuum source may be adapted to generate a negative-pressure environment, relative to atmospheric pressure, within the valve assembly while the valve is in the first position.

As with the previous aspect, the valve assembly may include a series of internal channels, at least some of which house the valve so that the valve is movable from the first position to the second position. The valve, in one embodiment, is also movable from the first position to the second position against the force of a compressible member acting on a surface of the valve. Other features of this aspect are not detailed here, but may be found below in the detailed description.

BRIEF DESCRIPTION OF THE DRAWINGS

A more complete appreciation of the subject matter of the present invention(s) and of the various advantages thereof can be realized by reference to the following detailed description in which reference is made to the accompanying drawings in which:

FIG. 3 is a cross-sectional view of the valve assembly of FIG. 2 shown with the valve in an open or resting condition, while

DETAILED DESCRIPTION

In describing the preferred embodiments of the invention(s), specific terminology will be used for the sake of clarity. However, the invention(s) is not intended to be limited to any specific terms used herein, and it is to be understood that each specific term includes all technical equivalents, which operate in a similar manner to accomplish a similar purpose.

As an example, the term "distal," as used herein, means relatively farther from a user, while the term "proximal" means relatively closer. In addition, use of the term bone-graft material herein is intended to refer to natural bone-graft substances, such as allograft, autograft, or other natural bone substances, while the term bone-graft-substitute material is intended to refer to synthetic materials acting as a substitute for natural bone, such as hydroxyapatite, β-TCP, or the like. Vitoss® is an example of such a bone-graft-substitute material. Further, use of the term "fluid path" herein is intended to refer to any passageway in which a fluid may flow from one area to another, the fluid being any fluid, such as, for example, a liquid or air.

Figure 1:
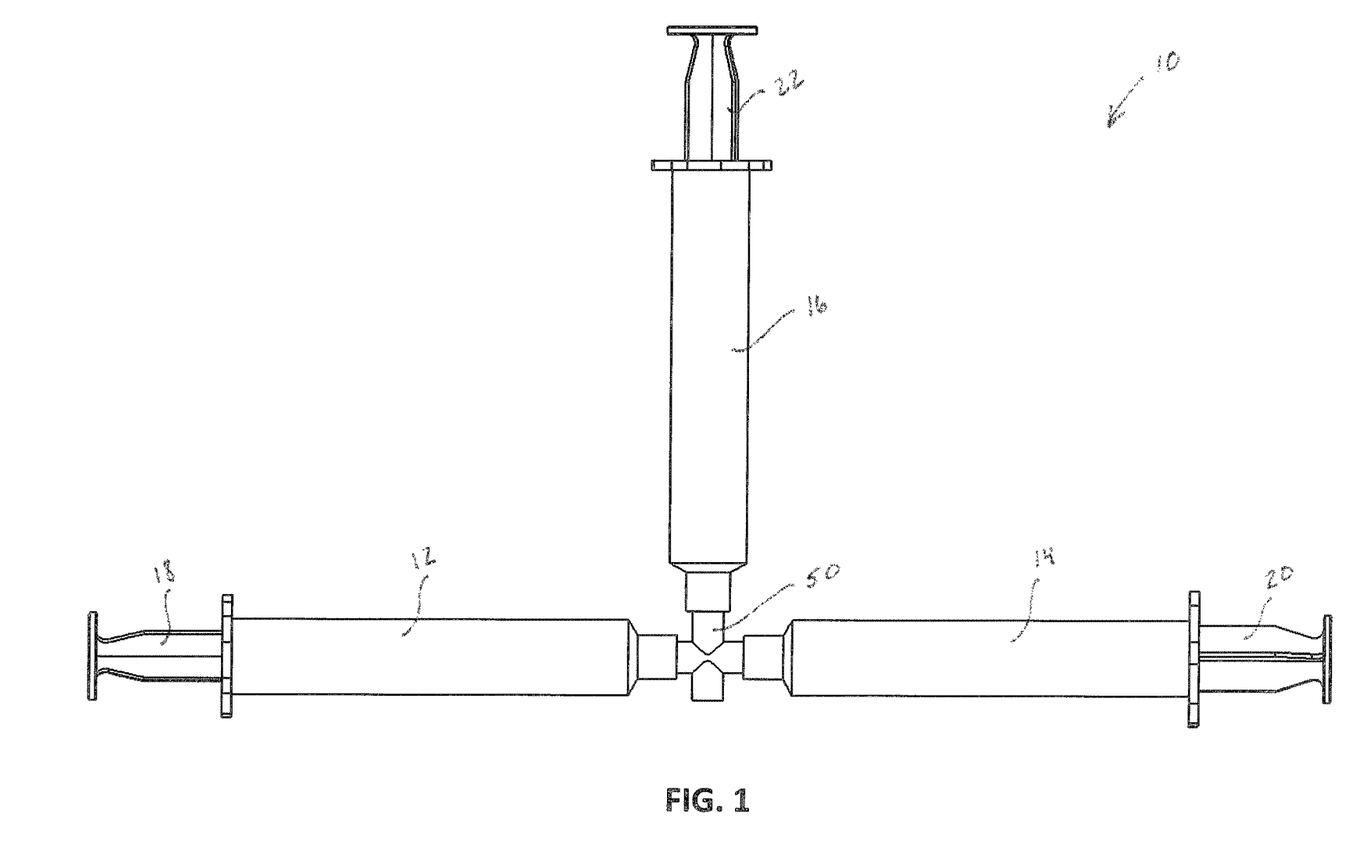
FIG. 1 is a side view of a mixing system, according to one embodiment of the present invention.

Referring to FIG. 1, a mixing system 10 is shown in which the system 10 comprises a set of syringes 12, 14, 16 connected, respectively, to a valve assembly 50 that allows mixing of components therein (e.g., bone-graft or bone-graft-substitute material along with other components, etc.) In one embodiment, syringe 12 may be filled with bone-graft or bone-graft-substitute material, such as Vitoss®, syringe 14 may be filled with a liquid, and syringe 16 may be used to create a vacuum and affect mixing between the components in syringes 12, 14. Thus, in use mixing system 10 may mix certain components of different bone-graft or bone-graft-substitute materials, or even other materials, with less steps and greater efficiency than prior systems.

Figure 2:
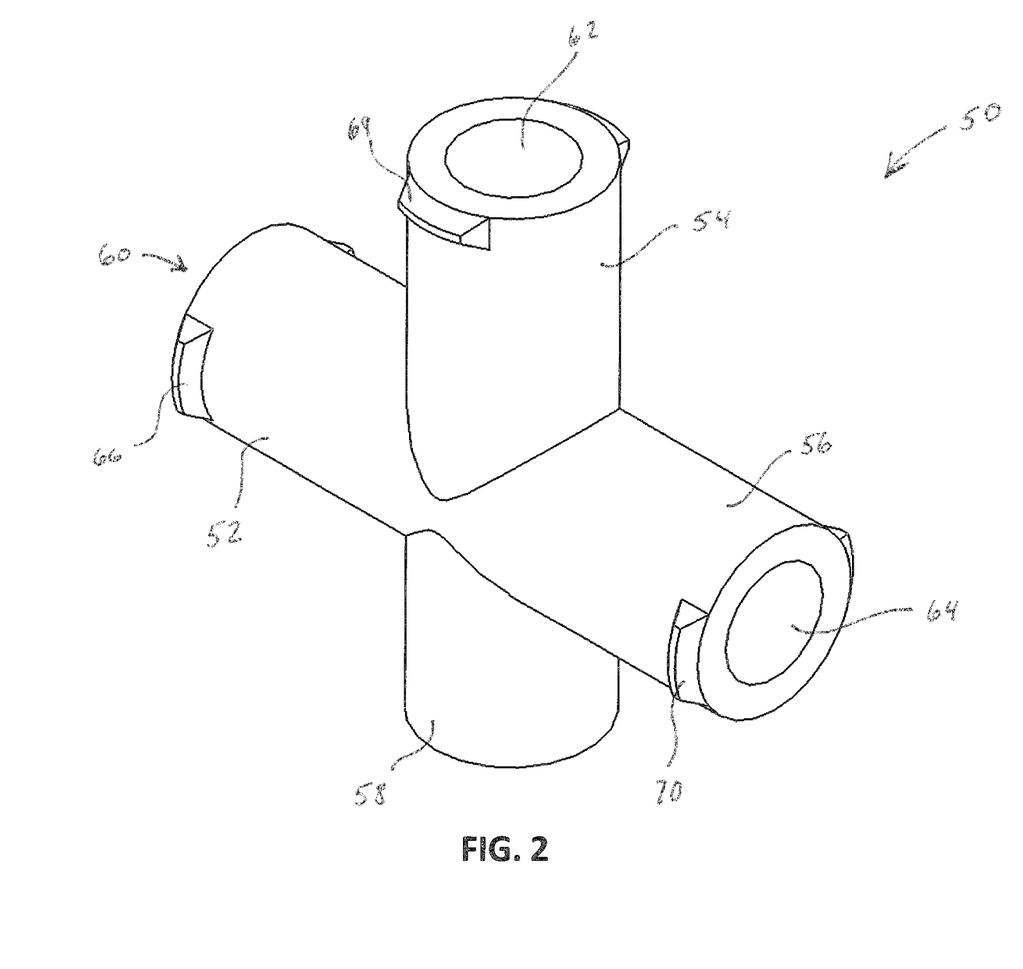
FIG. 2 is a perspective view of a valve assembly forming part of the mixing system of FIG. 1.

Turning to FIG. 2, valve assembly 50 may include a series of branches 52, 54, 56, 58 extending from its center, three (3) of which 52, 54, 56 may contain an opening 60, 62, 64 at an end thereof. In one embodiment, branch 58 of valve assembly 50 may be closed or sealed off, as shown. In addition, adjacent openings 60, 62, 64 may be a set of Luer fittings 66, 68, 70 adapted to mate with corresponding Luer structure formed on a portion of syringes 12, 14, 16 (described in detail below). In one embodiment, branches 52, 54, 56, 58 are a unitary structure that forms a cross-shape.

Figure 3:
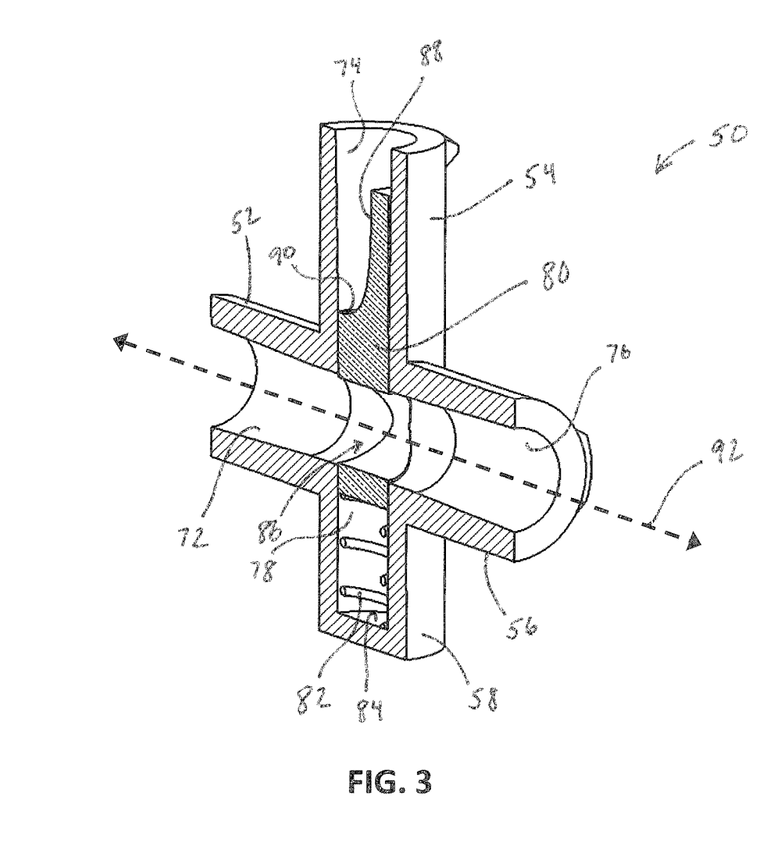

As shown in FIG. 3, branches 52, 54, 56, 58 of valve assembly 50 may also each include an internal bore or channel 72, 74, 76, 78, some of which 72, 74, 76 communicate with the atmosphere via openings 60, 62, 64. A valve 80 is also situated within assembly 50, in particular within internal bores 74, 78 of branches 54, 58, such that valve 80 is movable vertically within branches 54, 58. In one embodiment, valve 80 is engaged with a spring 82 arranged in internal bore 78 of branch 58, such that valve 80 may be compressed against spring 82. Spring 82 may, in some cases, be a helical compression spring that sits upon a floor surface 84 of branch 58 of valve assembly 50, such that spring 82 is wedged between valve 80 and floor surface 84. In other variants, spring 82 is simply a deformable or compressible material (e.g., a compressible solid) that compresses upon movement of valve 80 within internal bore 78 of branch 58. Stated differently, spring 82 may be any member suitable to allow movement of valve 80 within internal bore 78 and return valve 80 to its initial condition. In other embodiments, valve 80 itself may be a compressible structure, allowing movement of a portion of valve 80 vertically within branches 54, 58. Indeed, while spring 82 is referred to throughout the remainder of the disclosure, such reference is merely exemplary, as any of the aforementioned structures may achieve a similar function.

Figure 4:
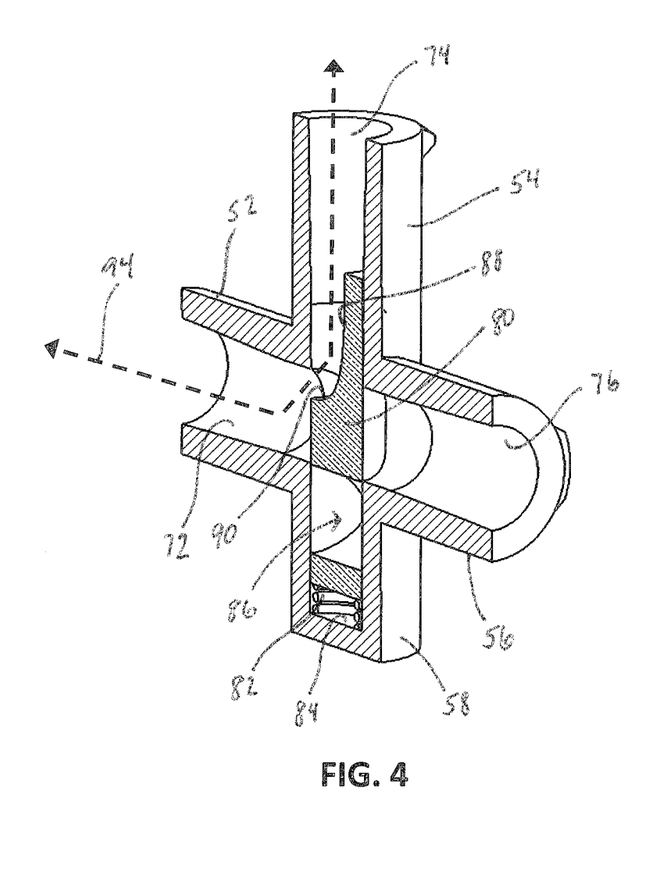
FIG. 4 is a cross-sectional view of the valve assembly of FIGS. 2-3 shown with the valve in an engaged position.

Valve 80 also includes at least one opening 86, in one embodiment, the opening 86 extending entirely through valve 80 to allow a fluid path 92 to be created (e.g., through internal bores 72, 76 of branches 52, 56 and opening 86 of valve 80). Referring now to FIG. 4, valve 80 may also include a recessed area 88 and a step 90 formed between recessed area 88 and the body of valve 80. Upon movement of valve 80 into internal bore 78 of branch 58 (e.g., via compression of spring 82), a separate fluid path 94 may be created along internal bores 72, 74 of branches 52, 54. Further, recessed area 88 and step 90 of valve 80 may serve to redirect fluid upon the proper path 94, while the remainder of valve 80 may block fluid transfer into other branches 56, 58 of valve assembly 50 while fluid path 94 is open. Stated differently, due to the geometry of valve 80, when fluid path 94 is opened, fluid path 92 through branches 52, 56 and opening 86 of valve 80 may be closed or sealed. This is due, at least, to the fact that opening 86 may be entirely positioned within internal bore 78 of valve assembly 50 once fluid path 94 is opened (e.g., via movement of valve 80 into branch 58 through compression of spring 82).

Figure 5A:
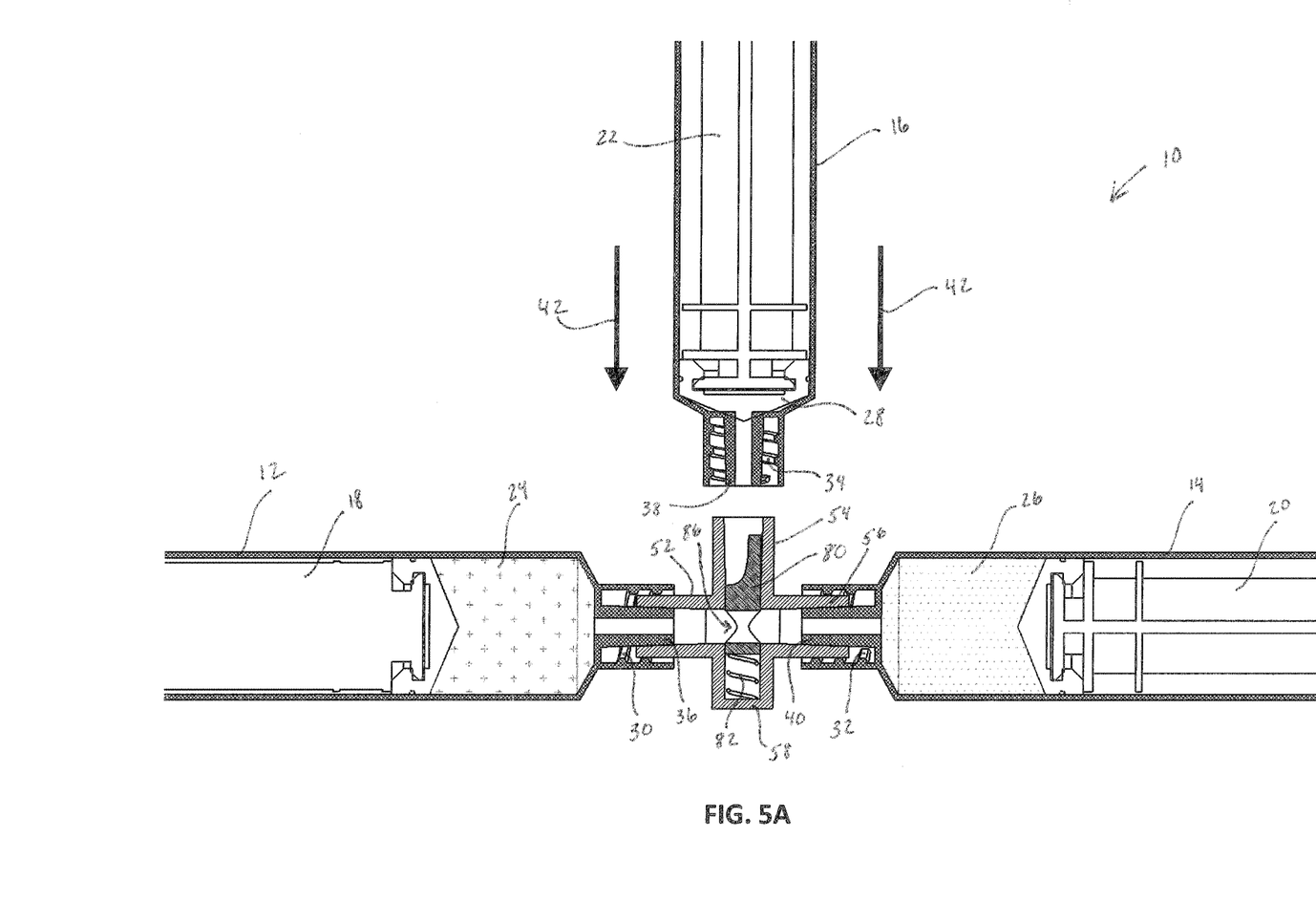
FIGS. 5A-B are cross-sectional views of the mixing system of FIG. 1 showing the vacuum syringe as being engaged to the valve assembly.

As shown in FIG. 5A, valve assembly 50 may also be connectable to syringes 12, 14, 16 by way of Luer fittings 66, 68, 70 on branches 52, 54, 56. Indeed, a distal end of each syringe 12, 14, 16 may include a nozzle 36, 38, 40 and a surrounding cylindrical wall with internal Luer structure 30, 32, 34 for engaging with Luer fittings 66, 68, 70 of valve assembly 50. Thus, a user may simply screw each syringe 12, 14, 16 on branches 52, 56, 54, respectively, to engage syringes 12, 14, 16 with valve assembly 50. In one embodiment, Luer connections 30, 32, 34 on syringes 12, 14, 16, may comprise internal threading (as is known in the art), and Luer fittings 66, 68, 70 on valve assembly 50 may be a lip(s) projecting from branches 52, 54, 56 for engaging with such threading. Once syringes 12, 14, 16 are connected to valve assembly 50, as described above, mixing system 10 may be constructed and ready for operation.

One embodiment of a method of utilizing mixing system 10 to mix bone-graft or bone-graft-substitute material 24 with a liquid 26 will now be described in connection with FIGS. 5A-G.

Initially, a user may place a certain amount of bone-graft or bone-graft-substitute material 24 within syringe 12. This may be done, alternatively, during manufacture of syringe 12. In one embodiment, the bone-graft or bone-graft-substitute material 24 may be in particulate form according to one or more of the following sizes (or a combination thereof): (1) morsel—about two to about four millimeters (≈2-4 mm) in diameter; (2) micro-morsel—about one to about two millimeters (≈1-2 mm) in diameter; and/or (3) fine particulate—less than about one millimeter (<≈1 mm) in diameter. Other particulate sizes for bone-graft or bone-graft-substitute material 24 are also contemplated, of course. Further, bone-graft or bone-graft-substitute material 24 may be mixed with one or more of a number of materials, such as gelatin, collagen, micro-fibrillar collagen, or the like. In a particular embodiment, the micro-fibrillar collagen used may be any of the collagen compositions detailed in U.S. Pat. Nos. 6,096,309 and 6,280,727, the disclosures of which are hereby incorporated by reference herein.

It is also noted that a Vitoss® product may be placed in syringe 12 as material 24. Indeed, material 24 may be a Vitoss® product in morsel, micro-morsel, and/or fine particulate form along with or apart from gelatin, collagen, micro-fibrillar collagen, or the like. In a preferred embodiment, bone-graft or bone-graft-substitute material 24 is a Vitoss® product, in fine particulate form, which is mixed with gelatin, collagen, and/or micro-fibrillar collagen and then lyophilized into a composite material in morsel, micro-morsel, and/or fine particulate form. Such composite particles of material 24, in this embodiment, may also have a size range of anywhere between about zero to about ten millimeters (≈0-10 mm) in diameter, with a preferred size range of anywhere between about five one-hundredths to about three millimeters (≈0.5-3 mm) in diameter. The bone-graft or bone-graft-substitute material(s) 24, according to this or other embodiments, can also include bioactive glass, as with several of the Vitoss® products (e.g., Vitoss® BA2X Bone Graft Substitute, etc.) The bioactive glass may be either solid or porous, and may have a size range of anywhere between about thirty two to about one-hundred fifty microns (≈32-150 μm) in diameter.

Certain Vitoss® compositions, any of which may encompass material 24, are described in detail in U.S. Pat. Nos. 6,383,519 and 6,521,246, the disclosures of which are hereby incorporated by reference herein. Further, the particular Vitoss® composition utilized, in one embodiment, may be modified or combined with various natural and synthetic polymers, film-forming materials, resins, slurries, aqueous mixtures, pre-polymers, organic materials, metals, and other adjuvants. In particular, materials such as collagen, wax, glycerin, gelatin, polycaprolactone, carboxymethylcellulose, pre-polymeric materials (e.g., precursors to various nylons, acrylics, epoxies, polyalkylenes, and the like), may permeate all or part of material 24, which may be formed in accordance with the '519 and '246 Patents. The bone-graft or bone-graft-substitute material 24 of the present invention can also include any of the shaped bodies disclosed in U.S. Pat. Nos. 7,189,263, 7,531,004, and 8,303,967, the disclosures of which are hereby incorporated by reference herein.

Once a particular bone-graft or bone-graft-substitute material 24 is placed within syringe 12, syringe 12 may be connected to valve assembly 50 by engaging its Luer structure 30 with the corresponding Luer fitting 66 on branch 52. Then (or alternatively before or at the same time), liquid 26 may be placed in syringe 14. Liquid 26, in certain embodiments, may be water, saline, blood, bone-marrow aspirate, platelet-rich plasma (PRP), certain sugar or salt solutions, such as potassium and dextrose solutions, or any combination thereof. Liquid 26 may also contain antibiotics, bone morphogenic proteins (BMPs), or other drugs or biologics. Syringe 14 is then connected to valve assembly 50 at branch 56 by way of its Luer connection 32 and the corresponding Luer fitting 70 on branch 56.

As shown by arrows 42 in FIG. 5A, syringe 16, which may be empty and include a plunger 22 that is fully or almost fully depressed, is subsequently connected to valve assembly 50 at branch 54, in particular through its Luer connection 34 and the corresponding Luer fitting 68 on branch 54. This connection is shown in detail in FIG. 5B. Prior to full engagement of syringe 16 to valve assembly 50 (which is shown in progress in FIG. 5B), valve 80 may be in its resting condition in which spring 82 supports valve 80 so that opening 86 and internal bores 72, 76 of branches 52, 56 are in fluid connection. Yet, as the internal space within valve assembly 50 (e.g., the space within internal bores 72, 76 and opening 86) is at virtually the same pressure as the space within either of syringes 12, 14, no automatic fluid transfer occurs at this stage (absent depression of one of plungers 18, 20 of syringes 12, 14, of course). Stated differently, bone-graft or bone-graft-substitute material 24 and liquid 26 may not mix at this stage (e.g., within valve assembly 50 or one of syringes 12, 14) since there is nothing to exert either material 24, 26 into valve assembly 50 or syringes 12, 14 (again, absent actuation of plungers 18, 20). The system 10 is simply static.

Figure 5B:
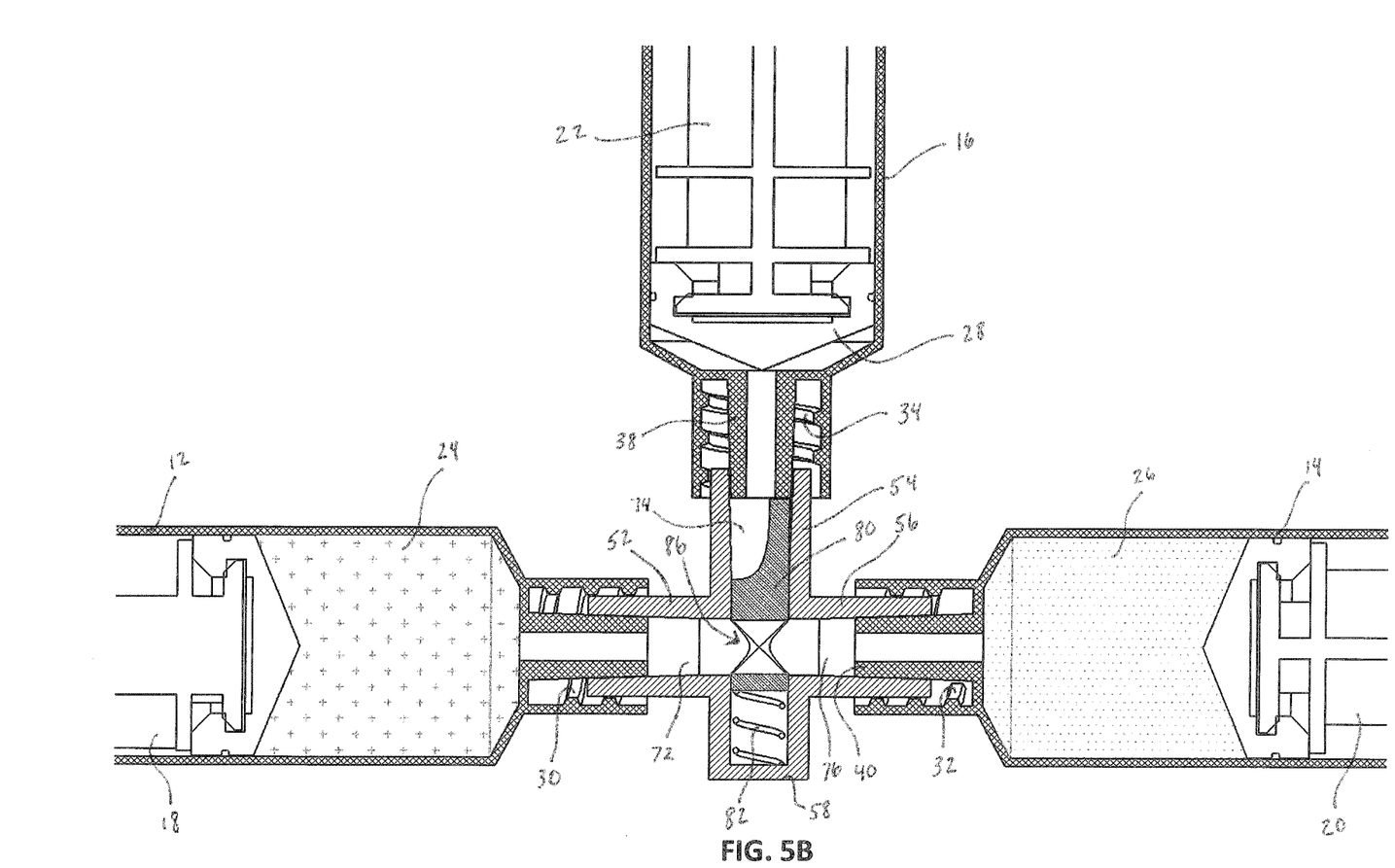
Figure 5C:
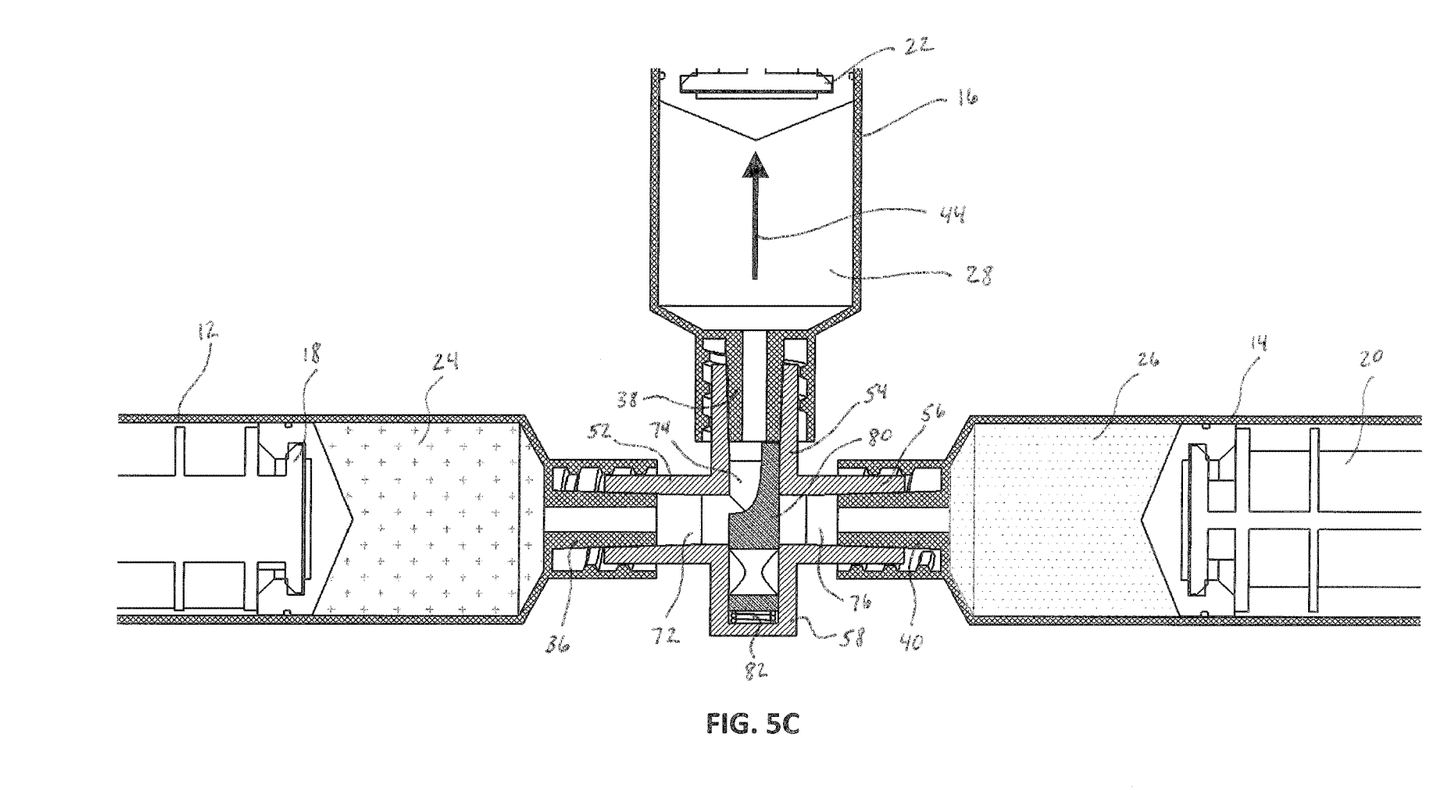
FIGS. 5C-D are cross-sectional views of the mixing system of FIG. 1 showing the plunger of the vacuum syringe being withdrawn to create a vacuum between the vacuum syringe and the morsel or bone-graft syringe.

As illustrated in FIGS. 5B and 5C, the user may then fully engage syringe 16 with branch 54 of valve assembly 50, such that nozzle 38 of syringe 16 presses on a portion of valve 80 to cause valve 80 to move within branch 58 (e.g., through compression of spring 82 against floor surface 84). During such movement of valve 80, opening 86 may be situated entirely within branch 58, such that fluid path 92 is closed off and a fluid path 94 (FIG. 5D) is created between syringes 12, 16. In particular, fluid path 94 may be created through nozzle 38 of syringe 16, internal bore 74 of branch 54, recessed area 88 and step 90 of valve 80, internal bore 72 of branch 52, and finally nozzle 36 of syringe 12. In an alternate embodiment, syringe 16 may be fully engaged with valve assembly 50, and valve 80 moved fully within branch 58 to open fluid path 94, before connection of liquid syringe 14 with valve assembly 50. In this manner, liquid syringe 14 may initially be sealed off from interaction with syringe 12 so that absolutely no transfer of liquid 26 to syringe 12 occurs.

Figure 5D:
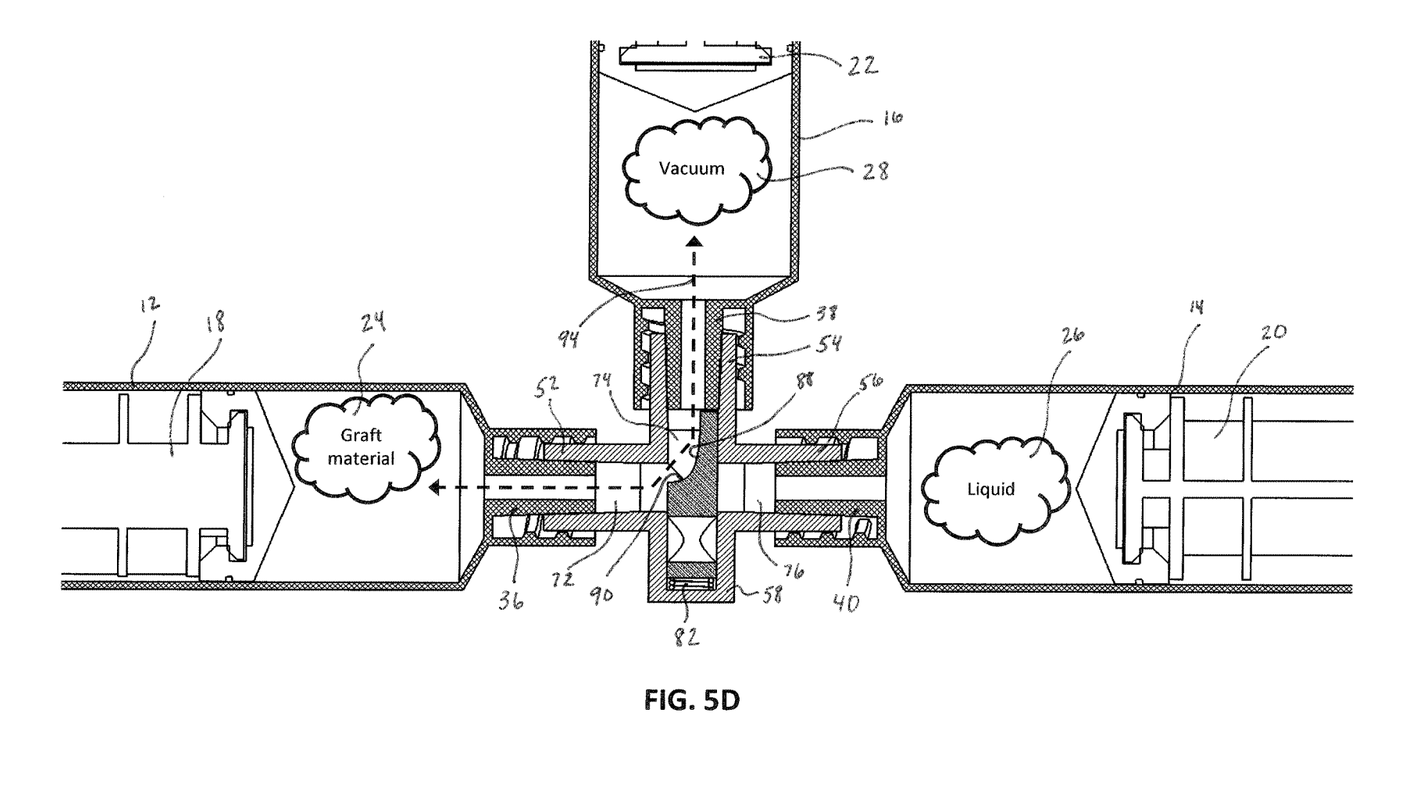
Figure 5E:
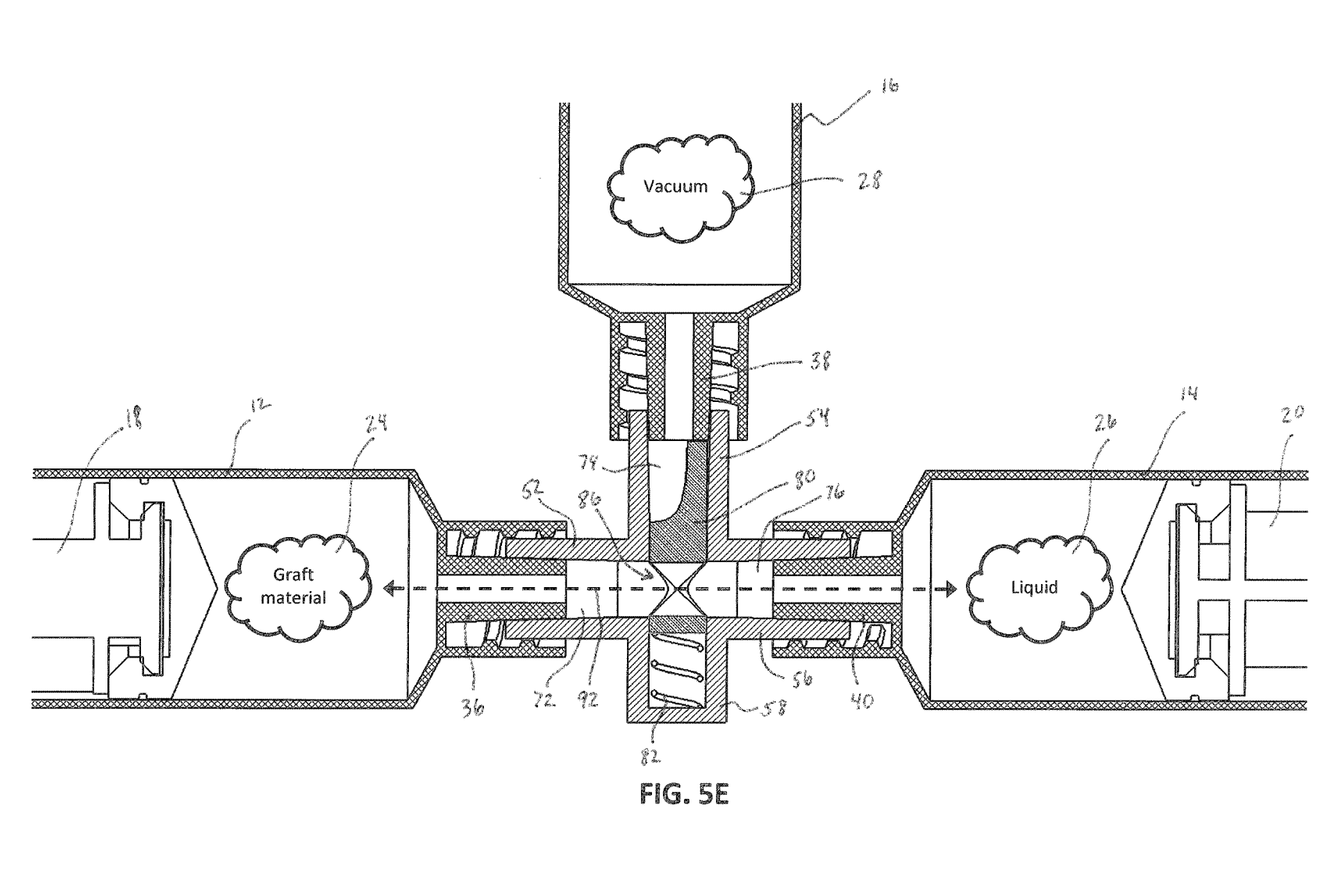
FIG. 5E is cross-sectional view of the mixing system of FIG. 1 with a fluid path being created between the morsel or bone-graft syringe and the liquid syringe (e.g., through the valve assembly of FIGS. 2-4).

With fluid path 94 opened, the user may retract plunger 22 of syringe 16 in the direction of arrow 44 in FIG. 5C to create a vacuum 28 amongst syringes 12, 16 and valve assembly 50. Stated another way, retraction of plunger 22 in the direction of arrow 44 may create a negative-pressure environment within the body of valve assembly 50 and syringes 12, 16 (vacuum 28 illustrated in FIGS. 5D-E is intended to indicate that syringe 16 is used to create negative pressure amongst assembly 50 and syringes 12, 16, and not to indicate that vacuum 28 is only present in syringe 16). Thus, the space within nozzles 36, 38 and branches 52, 54 may be subject to a lower pressure than the atmosphere once plunger 22 of syringe 16 is retracted. In this manner, a vacuum 28 may be created amongst syringes 12, 16 and valve assembly 50 so that negative pressure exists in those areas. Due to the fact that bone-graft or bone-graft-substitute material 24 may be in lyophilized composite form (e.g., Vitoss® mixed with gelatin, collagen, micro-fibrillar collagen, or the other such material(s), and then lyophilized), however, material 24 may not be movable through nozzle 36 of syringe 12 absent saturation with liquid 26. Thus, once vacuum 28 is created, material 24 may not be forced from syringe 12 through nozzle 36. Rather, material 24 may simply remain in syringe 12 while being subject to pressure from vacuum 28.

With a negative-pressure environment present in valve assembly 50, syringe 16 may be withdrawn proximally along branch 54 of valve assembly 50 (e.g., unscrewed from branch 54), as shown in FIG. 5E. Indeed, syringe 16 may be moved proximally by a distance sufficient to allow valve 80 to move out of branch 58 via pressure exerted thereon by spring 82, thus causing opening 86 of valve 80 to align with internal bores 72, 76 of branches 52, 56. Portions of valve 80, once moved proximally, may also seal off internal bore 74 of branch 54 from the remaining branches 52, 56, 58 so that the vacuum 28 or internal negative pressure within valve 50 is maintained. In addition, since syringe 14 was not previously subject to the effects of vacuum 28, and is therefore at a pressure roughly equal to the existing atmospheric pressure, liquid 26 may be forced from syringe 14 into valve assembly 50 along fluid path 92. Stated differently, as the pressure in syringe 14 is greater than the pressure within valve assembly 50 (e.g., via the effects of vacuum 28), liquid 26 will tend to be forced from syringe 14 and into valve assembly 50 so that both pressures equalize. Also, since syringe 12 is at virtually the same internal pressure as valve assembly 50, liquid 26 may be forced into syringe 12 along fluid path 92 so that bone-graft or bone-graft-substitute material 24 is fully saturated with liquid 26, which in some cases may be water, saline, blood, bone marrow aspirate, PRP, certain sugar or salt solutions, or a combination thereof. As such, an initial mixing of material 24 and liquid 26 may take place within syringe 12 so that bone-graft or bone-graft-substitute material 24 gains greater bio-affinity by way of saturation with liquid 26. If desired, plunger 20 of syringe 14 may also be depressed in this sequence to further assist with transferring liquid 26 into syringe 12 to mix with material 24. Since material 24 is saturated with liquid 26 during this step, as discussed above, material 24 may also become more fluid so that it may easily exit syringe 12 via nozzle 36. Stated differently, while prior to this step it may have been difficult to force material 24 from syringe 12 due to its solid or near-solid state (e.g., as a lyophilized composite composed of morsels, micro-morsels, or fine particulate Vitoss® mixed with any of the previously-described components, such as gelatin, collagen, micro-fibrillar collagen, or the like), after saturation with liquid 26 material 24 may be less viscous so that material 24/liquid 26 may be removed from syringe 12 through nozzle 36. In one embodiment, after saturation with liquid 26, material 24 may become a viscous gel, or a pliable mass of material that is able to freely travel through nozzle 36 of syringe 12, valve assembly 50, and/or syringe 14.

Figure 5F:
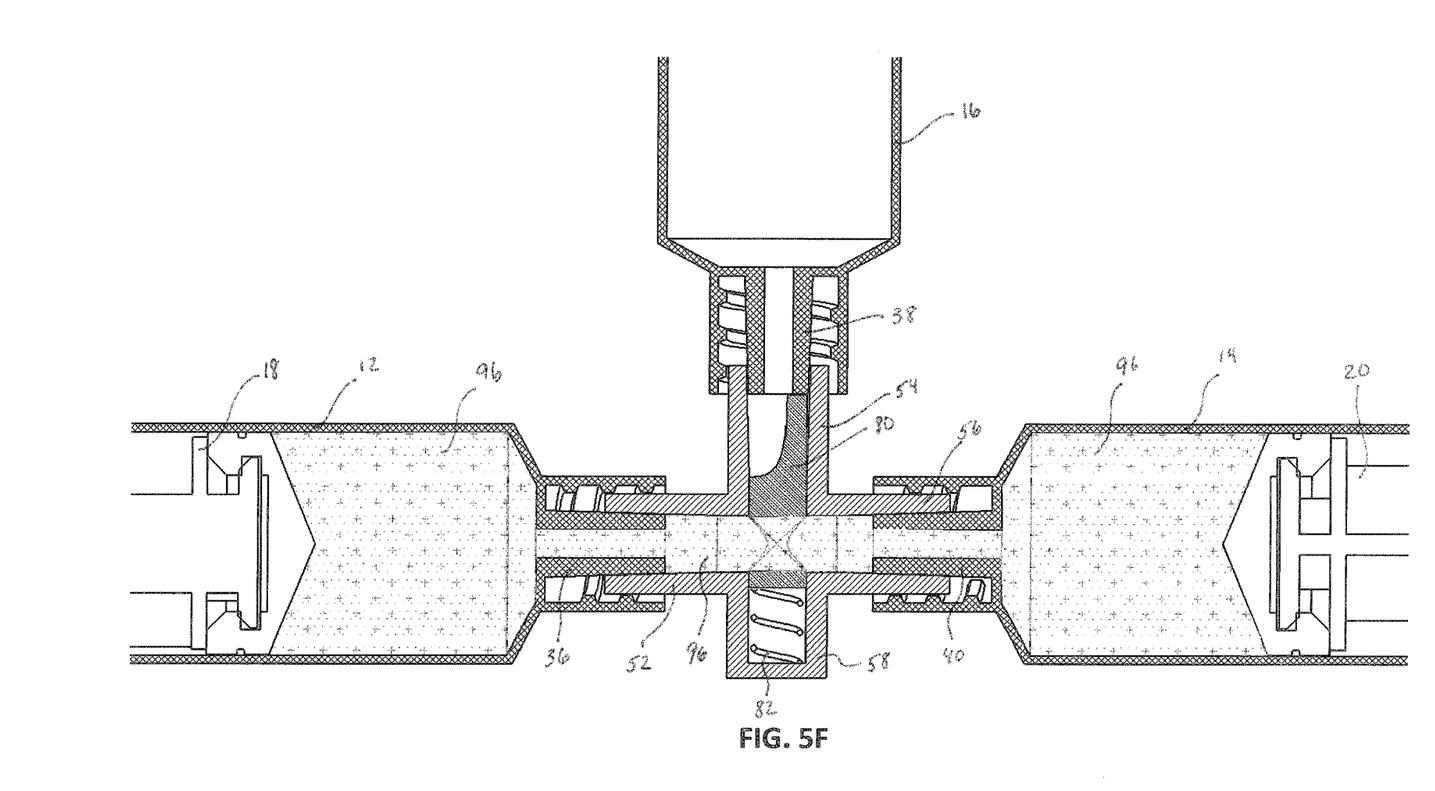
FIGS. 5F-G are cross-sectional views of the mixing system of FIG. 1 with mixing occurring between the morsel or bone-graft syringe and the liquid syringe.

Actuation of plungers 18, 20, at this stage, may cause yet additional mixing to occur along fluid path 92, as shown in detail in FIG. 5F. A mixture of material 24 and liquid 26 may then be created, such that material 24 is fully saturated or wetted with liquid 26, as represented by mixture 96 in FIG. 5F. During mixing to create mixture 96, certain portions of bone-graft or bone-graft-substitute material 24 (e.g., Vitoss® mixed with gelatin, collagen, and/or micro-fibrillar collagen and then lyophilized) may dissolve or otherwise combine with fluid 26 so that mixture 96 ultimately achieves the optimal viscosity to travel through the various components of system 10. Indeed, in a preferred embodiment, Vitoss® particles may form a core of the lyophilized material 24, with gelatin, collagen, and/or micro-fibrillar collagen forming the exterior, and the exterior may dissolve or otherwise combine with liquid 26 once material 24 is wetted with liquid 26. In this manner, the Vitoss® particles forming part of material 24 (which in some embodiments are in fine particulate form) may be smaller than the lyophilized composite material 24. Thus, upon dissolving portions of the exterior of material 24 (e.g., gelatin, collagen, and/or micro-fibrillar collagen), the surviving Vitoss® core may more easily transfer amongst syringes 12, 14 and valve assembly 50 due to its size. As noted previously, the surviving core of Vitoss® may also include bioactive glass (porous or non-porous), of course.

The user, at his or her election, may transfer mixture 96 back and forth between syringes 12, 14 as many times as necessary to achieve full mixing of material 24 and fluid 26. In this manner, bone-graft or bone-graft-substitute material 24 may be adequately saturated with liquid 26 to create mixture 96 for application in many different surgical contexts, as detailed previously. If desired, during the mixing process syringe 16 may also be fully removed from connection with valve assembly 50, as shown in FIG. 5G, although this is not required.

Figure 5G:
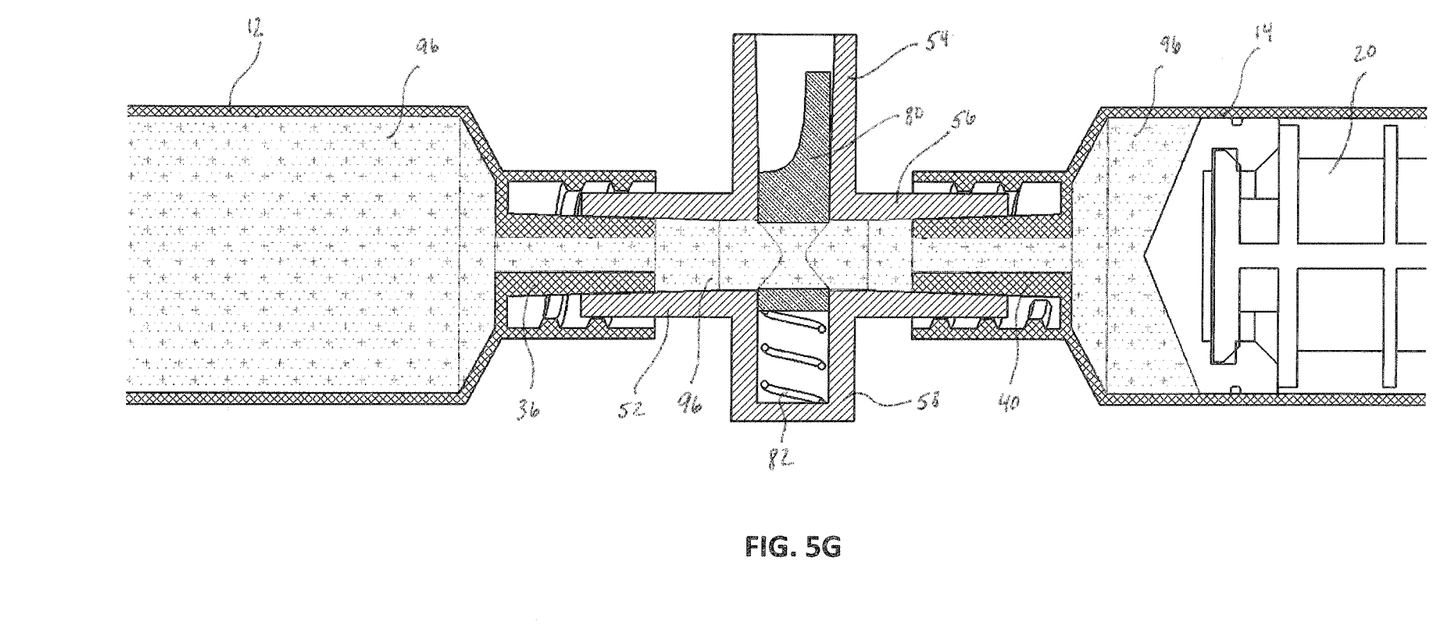

At the end of mixing, as shown in FIG. 5G, mixture 96 may be transferred entirely to one of syringes 12, 14 (the transfer is shown as being to syringe 12 in FIG. 5G) so that mixture 96 may be applied at the surgical site to create efficient bone growth or bone reformation. Thus, as described, mixing system 10 allows a user to more efficiently mix components of a bone-graft or bone-graft-substitute material for application in different surgical fields.

In the devices shown in the figures, particular structures are shown as being adapted for use in the mixing of certain substances according to the present invention(s). The invention(s) also contemplates the use of any alternative structures for such purposes, including structures having different lengths, shapes, and/or configurations. For instance, although syringe 16 is disclosed as being utilized to create a vacuum 28 by manual means (e.g., retraction of plunger 22), it is contemplated that any vacuum means may be used, including an automated or electronic vacuum means. Thus, using such automated or electronic vacuum means, any level of vacuum (within certain limits, of course) may be created amongst syringes 12, 16 and valve assembly 50. As such, additional negative pressure may be created in those areas so that, once valve 80 is returned to its resting condition via the removal of syringe 16 from connection with valve assembly 50, liquid 26 may more easily flow from syringe 14 to syringe 12 along fluid path 92.

It is also the case that branch 56 (or any of the branches 52, 54, 56) may include a needleless valve to seal branch 56 when nozzle 40 of syringe 14 is not pushed through the needleless valve. Such structure may be beneficial in creating yet additional vacuum pressure in system 10. For instance, it is contemplated that, in one embodiment, syringes 12, 16 may be connected to valve assembly 50, fluid path 94 opened (FIG. 5D), and vacuum 28 created via retraction of plunger 22, but during this process syringe 14 may not be connected to valve assembly 50. Rather, branch 56 may be sealed from the atmosphere via a needleless valve so that syringe 16 may be retracted from connection with valve assembly 50 (FIG. 5E), but no fluid path 92 is created. Instead, plunger 22 of syringe 16 may be depressed once more, syringe 16 reconnected to valve assembly 50, and the vacuum process repeated (FIGS. 5C-D) to create additional vacuum pressure 28 amongst syringes 12, 16 and valve assembly 50. Then, syringe 14 may ultimately be connected to valve assembly 50 through the needleless valve within branch 56, fluid path 92 opened (FIG. 5E), and mixing may take place under additional vacuum pressure 28. Thus, such a method provides an alternate means to generate further vacuum pressure 28 within mixing system 10.

In the various vacuum pressure 28 generating steps discussed above, it is also possible to utilize a vacuum-lock syringe as syringe 16. In other words, syringe 16 may include locking structure to maintain plunger 22 in its retracted position once vacuum 28 is created. As one example, plunger 22 may be retracted to create vacuum 28, and then rotated to a locked position so that vacuum 28 is maintained, at which point syringe 16 may be removed or withdrawn proximally along branch 54 to open fluid path 92 for mixing of material 24 and liquid 26.

For exemplary purposes, branches 52, 54, 56, 58 of valve assembly 50 are depicted with substantially equivalently sized diameters and internal bores 72, 74, 76, 78. However, it is envisioned that they may have different sizes. For instance, branches 54, 58 and their internal bores 74, 78 may have larger diameters than branches 52, 56 and their internal bores 72, 76, such that valve 80 may be large enough to accommodate an opening 86 that is equal in diameter to internal bores 72, 76 while maintaining structural integrity of the valve 80.

As yet another example, in one embodiment branches 52, 56 of valve assembly 50, in particular internal bores 72, 76 thereof, may include baffles or other mixing structure to assist with mixing of material 24 and liquid 26 during transfer between syringes 12, 14. Further, although a spring 82 is shown in the figures, alternate compressible structures may be used, so long as opening 86 of valve 80 may be entirely encompassed within branch 58 to create the various fluid paths 92, 94. Stated differently, any compressible structure (including a compressible valve 80) may be used in place of spring 82 so long as the structure allows movement of valve 80 within branch 58 to open fluid path 94 and seal fluid path 92, and also return valve 80 to its resting condition in which fluid path 92 is open and fluid path 94 is sealed.

Alternates to valve 80 may also be used with system 10. For example, in one embodiment valve 80 may not include opening 86, but rather may be movable vertically within branch 54 to a degree such that fluid path 92 is opened. Indeed, spring 82 may be larger than in the previous embodiments, and valve 80 (without opening 86) may be movable within branch 54 so that a bottom surface of valve 80 is situated above internal bores 72, 76 of branches 52, 56. In this manner, a portion of spring 82 supporting valve 80 may be situated at the intersection of branches 52, 54, 56, 58, valve 80 may be positioned above such intersection, and fluid path 92 may be opened so that liquid 26 and/or material 24 can travel under valve 80 and through spring 82.

As a further example, the Luer structure utilized with mixing system 10 (e.g., on syringes 12, 14, 16 and valve assembly 50) may be omitted, if desired, and syringes 12, 14, 16 may simply be press-fit onto branches 52, 54, 56 of valve assembly 50. In other words, nozzles 36, 38, 40, along with their external cylindrical walls, may be configured to form a friction fit with branches 52, 54, 56 so that syringes 12, 14, 16 can be connected to valve assembly 50 to affect mixing of material 24 and liquid 26, as described above.

It should be noted, as well, that in certain embodiments valve 80 may be rotatable within assembly 50, such that a fluid path (not shown) may be created through internal bores 74, 76 of branches 54, 56. In such an embodiment, valve 80 may be lockable in one orientation (e.g., to create fluid path 94), rotatable to a second orientation in which a separate fluid path (not shown) is created along internal bores 74, 76, and lockable in the second orientation to maintain the integrity of the fluid path.

Also, while certain steps of the above-described method(s) may have been discussed in a particular order, it is to be understood that the order may be altered in any manner suitable to mix the substances discussed previously. Thus, the order of steps for the method(s) is not essential, and such order may be varied or changed in any manner considered suitable by one of skill in the art.

Although the invention(s) herein has been described with reference to particular embodiments, it is to be understood that these embodiments are merely illustrative of the principles and applications of the present invention(s). It is therefore to be understood that numerous modifications may be made to the illustrative embodiments and that other arrangements may be devised without departing from the spirit and scope of the present invention(s) as defined by the appended claims.

It will also be appreciated that the various dependent claims and the features set forth therein can be combined in different ways than presented in the initial claims. It will also be appreciated that the features described in connection with individual embodiments may be shared with others of the described embodiments.

The invention claimed is:

1. A system for mixing a bone-graft or bone-graft-substitute material with one or more other components, the system comprising:
    a source of bone-graft or bone-graft-substitute material, a liquid source, and a vacuum source; and
    a valve assembly configured so that the source of bone-graft or bone-graft-substitute material, the liquid source and the vacuum source are in communication with the valve assembly, the valve assembly having a valve movable between a first position in which a first fluid passageway is created between the source of bone-graft or bone-graft-substitute material and the vacuum and a second position in which a second fluid passageway is created between the source of bone-graft or bone-graft-substitute material and the liquid source,
    wherein the valve assembly includes a plurality of internal channels, at least one of which houses the valve,
    wherein the valve includes a first surface that defines a boundary of the first fluid passageway when the valve is in the first position, a second surface having an entirely inward facing surface area that defines a boundary of the second fluid passageway when the valve is in the second position, the second surface outside of the first fluid passageway when the valve is in the first position, and a third surface having an outward facing surface area that separates the first and second surfaces, the third surface configured to contact a wall of the valve assembly defining a boundary of at least one of the plurality of inner channels,
    wherein, in the second position, the valve seals off the first fluid passageway, and
    wherein the vacuum source is adapted to generate a negative-pressure environment, relative to atmospheric pressure, within the valve assembly while the valve is in the first position.

2. The system of claim 1, wherein the first surface is curved in a manner such that a first end is approximately parallel to a longitudinal axis of a syringe providing a vacuum source and a second end is transverse to the first end.

3. The system of claim 1, wherein the valve assembly further comprises first, second and third branches, each branch including one of the plurality of internal channels and configured to connect the valve assembly to one of the source of bone-graft or bone-graft-substitute material, a liquid source, and a vacuum source, the first and second branches being parallel to one another and configured for engagement to the source of bone-graft or bone-graft substitute material and liquid source, respectively.

4. The system of claim 3, wherein the valve assembly further comprises a fourth branch, the fourth branch being parallel to the third branch and having a closed end, the third branch including a portion of the valve disposed therein.

5. The system of claim 4, wherein the valve includes a portion disposed in the fourth branch that moves when the valve moves from the first position to the second position.

6. The system of claim 1, wherein the source of bone-graft or bone-graft-substitute material, the liquid source, and the vacuum source are syringes connected to the valve assembly.

7. The system of claim 1, wherein the bone-graft or bone-graft-substitute material comprises natural bone particles, particles of β-TCP, or hydroxyapatite combined with β-TCP, each of such materials optionally including bioactive glass, and the liquid source comprises water, saline, blood, bone marrow aspirate, or a combination thereof.

8. The system of claim 1, wherein the vacuum source is a syringe and the valve moves automatically upon attachment of the syringe to the valve assembly.

9. A system for mixing a bone-graft or bone-graft-substitute material with one or more other components, the system comprising:

a source of bone-graft or bone-graft-substitute material, a liquid source, and a vacuum source; and a valve assembly configured so that the source of bone-graft or bone-graft-substitute material, the liquid source and the vacuum source are in communication with the valve assembly, the valve assembly having a valve movable between a first position in which a first fluid passageway is created between the source of bone-graft or bone-graft-substitute material and the vacuum and a second position in which a second fluid passageway is created between the source of bone-graft or bone-graft-substitute material and the liquid source, wherein the valve assembly includes a plurality of internal channels, at least one of which houses the valve, wherein the vacuum source is adapted to generate a negative-pressure environment, relative to atmospheric pressure, within the valve assembly while the valve is in the first position, wherein the valve includes an opening therethrough from a first side of the valve to a second side of the valve opposite the first side, the opening defined by a rounded interior wall of a singular cross-sectional size from the first side to the second side such that fluid communication between the first side and the second side occurs when the valve is in the second position and such fluid communication is contained within the rounded interior wall, wherein, in the first position, the rounded interior wall is outside of the first fluid passageway, and wherein, in the second position, the valve seals off the first fluid passageway.

* * * * *